US008761873B2

(12) United States Patent
Wheeler et al.

(10) Patent No.: US 8,761,873 B2
(45) Date of Patent: Jun. 24, 2014

(54) NEURAL PROSTHESIS SYSTEM AND METHOD OF CONTROL

(75) Inventors: Christa Wheeler, Cleveland Heights, OH (US); Paul Hunter Peckham, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 770 days.

(21) Appl. No.: 12/865,362

(22) PCT Filed: Jan. 30, 2009

(86) PCT No.: PCT/US2009/032702
§ 371 (c)(1),
(2), (4) Date: Jul. 29, 2010

(87) PCT Pub. No.: WO2009/097563
PCT Pub. Date: Aug. 6, 2009

(65) Prior Publication Data
US 2011/0004118 A1 Jan. 6, 2011

Related U.S. Application Data

(60) Provisional application No. 61/024,789, filed on Jan. 30, 2008.

(51) Int. Cl.
*A61N 1/08* (2006.01)
*A61N 1/36* (2006.01)
(52) U.S. Cl.
CPC .................................. *A61N 1/36003* (2013.01)
USPC .................................................. 607/2; 607/48

(58) Field of Classification Search
CPC .................................................. A61N 1/36003
USPC .................................................. 607/2, 48, 49
See application file for complete search history.

(56) References Cited

U.S. PATENT DOCUMENTS

| 6,839,594 B2 * | 1/2005 | Cohen et al. .................... 607/48 |
| 2001/0000187 A1 * | 4/2001 | Peckham et al. ................ 607/48 |
| 2003/0139783 A1 | 7/2003 | Kilgore et al. |
| 2005/0096521 A1 | 5/2005 | Andersen et al. |

OTHER PUBLICATIONS

International Search Report, issued on Mar. 11, 2009, in International Application No. PCT/US2009/032702.

* cited by examiner

*Primary Examiner* — Christopher D Koharski
*Assistant Examiner* — Frances Oropeza
(74) *Attorney, Agent, or Firm* — Tarolli, Sundheim, Covell & Tummino LLP

(57) ABSTRACT

Multiple designs, systems, methods and processes for control using electrical signals recorded from clinically paralyzed muscles and nerves are presented. The discomplete neural prosthesis system and method for clinically paralyzed humans utilizes a controller. The controller is adapted to receive a volitional electrical signal generated by the human that is manifest below the lesion that causes the clinical paralysis. The controller uses at least the volitional electrical signal to generate a control signal that is output back to a plant to change the state of the plant, which in one aspect is one or more of the user's paralyzed muscles to achieve a functional result or to devices in the environment around the user that are adapted to receive commands from the controller.

16 Claims, 6 Drawing Sheets

500

NEURAL PROSTHESIS SYSTEM AND METHOD OF CONTROL

CROSS-REFERENCE TO RELATED APPLICATIONS

This application claims the benefit of U.S. application Ser. No. 61/024,789 filed 30 Jan. 2008.

Thus work was supported at least in part by the National institutes of Health (NIH) under NIH grant number T32-EB04314. Accordingly, the U.S. government may have certain rights herein. This work, was supported at least in part by the State of Ohio Biomedical Research Commercialization Program, Ohio Neurostimulation and Neuromodulation Partnership program.

TECHNICAL FIELD

The subject matter described herein relates to systems, and methods for control using electrical signals obtained from muscles and nerves that are clinically paralyzed.

BACKGROUND

Neurological trauma, dysfunction, or disease can leave persons with severe and life threatening motor or sensory disabilities that can compromise the ability to control basic vital functions. Persons with neurological impairments often rely on personal assistants, adaptive equipment and environmental modifications to facilitate their daily activities. Neural prostheses are highly effective methods for restoring Junction to individuals with neurological deficits by electrically manipulating the peripheral or central nervous systems. By passing small electrical currents through a nerve or directly to the motor units of a muscle via intramuscular, epimysial, and surface electrodes, neural prostheses can initiate action potentials which in turn trigger the release of chemical neurotransmitters to affect an end organ, such as a muscle. Techniques exist to selectively activate axons of any size or location within a nerve or fascicle, making it possible to preferentially target small sensory fibers or duplicate natural motor unit recruitment in order to minimize fatigue and grade the strength of a stimulated muscular contraction. In addition to exciting the nervous system, the proper current waveform and configuration of electrodes can block nerve conduction and inhibit action potential transmission. Thus, in principle any end organ normally under neural control is a candidate for neural prosthetic control.

Neural prostheses may consist of wholly external components with only limited surface or percutaneous electrical contacts, combinations of both external and implanted components or in some cases tally implanted systems with limited or no interface to components external to the body. In some cases, recording components of neural prostheses may interface with external systems that impact the user such as external mechanical orthotics or other devices. In further advances in the field of neural prosthesis, networked systems are developed whereby combinations of sensors and actuators are implanted within the user and networked into a common system. Some exemplary systems are described for example in U.S. Pat. No. 5,167,229 to Peckham, et. al., and U.S. Pat. No. 7,260,436 to Kilgore et. al.

Neural prostheses commonly operate in one of two separate control modes, open loop and closed loop, in the case of open loop control, the neural prostheses applies electrical signals to the body based on a pre-defined simulation, pattern that does not change after initiation based on the movement or change of body state. The pre-defined stimulation pattern is triggered using a variety of inputs, including joysticks, voice commands, or feedback from other sensors that provide information about the current state or orientation of the body and the user's desired state. Closed loop control modes use information about the stale of the user's body during stimulation to further resolve and tune the stimulation to achieve more accurate and precise motion. In order to Implement these various control modes, it is common for neural prostheses to use sensors to allow the user to issue command signals to the system and for estimating the body state, i.e. its position, orientation, force etc.

Existing neural prostheses utilize two different types of command signals, a logical or trigger command signal and a continuous or graduated control signal. The logical control signals are used to turn external devices on or off, initiate a predefined motion, or stimulation pattern, or cycle through a set of different patterns such as different grasp patterns such as lateral and palmer grasp in the case of an upper extremity neural prosthesis, and lock or unlock a device at various force levels. Examples of logical command signals include push button switches, reaching a specific threshold value with a command signal recorded from a part of the body, or holding a command signal at a certain threshold level for a predetermined length of time. A continuous command signal is required to control degree of motion or position and force applied by the neural prosthesis. Some examples of command signal sources include joint positions or potentiometer readings obtained from joints where the user retains volitional control, myoelectric signals obtained from muscles above the lesion where the user maintains functional control such as voluntary control over wrist extensor muscles by a tetraplegic user with a C6 level injury. The goal in the design of neural prostheses is to create command inputs that are a natural extension of the user's intact motor system, It is clear that neural prosthetic approaches can provide both therapeutic and functional benefits to individuals with impairments due to neurological injury or disorder. However, a significant disadvantage of prior neural prostheses is due to a lack of natural command signals that are easy for a user to internalize and use to command the neural prosthesis.

There is increasing evidence that even in eases of severe spinal trauma that result in clinically complete Spinal Cord Injuries (SCI) some axons remain intact across the lesion. Traditional techniques for assessing SCI involve manual muscle testing and sensory testing. These traditional techniques have a functional basis for evaluating whether or not volitional control exists; meaning volitional control below the lesion is measured by evaluating the force manifest by the muscle under volitional control of the injured subject. Thus an SCI is determined to be functionally or clinically complete based on the presence or absence of visible or palpable movement in the muscles below the lesion. In recent studies seeking to develop new diagnostic techniques to analyze lesions in clinically complete SCI it has been found that there exists sufficient numbers of axons that cross the lesion that allow volitional electrical signals that cross the lesion and be manifest below the lesion, even though the signals are not strong enough to cause visible muscle contraction. For example, the volitional electrical signal may incomplete innervate a muscle and thus not have the ability to trigger enough motor units to cause a physically manifest contraction of the muscle. However, this sub-functional activation of motor units within the muscle does result in a measurable electromyography (EMG) signals. Someone with an SCI injury or other injury or trauma to the nervous system that is functionally or clinically complete, with no clinically manifest movement of muscles below the lesion, but who upon closer analysis is found to still generate volitional electrical potentials in muscles and nerves below the lesion is referred to herein using the term discomplete neural lesion.

SUMMARY OF INVENTION

In one embodiment the present system and method provides a discomplete neural controller for a human with a discomplete neural lesion or discomplete SCI, referred to generally as a discomplete lesion, that accepts a volitional electrical potential generated by the human below the discomplete lesion. The volitional electrical potential is used by the system and method to generate a control signal, where the control signal is a function of the volitional electrical potential. That control signal is in turn applied to a plant. In another aspect, the volitional electrical potential is collected via an electrode. In still other aspects, the volitional electrical potential is measured and quantified by the controller and the measurement is used to modulate the control signal output to the plant.

In another embodiment the present system and method provides a discomplete neural prosthesis for a human with a discomplete neural lesion or discomplete SCI, referred to generally as a discomplete lesion, that accepts a volitional electrical potential generated by the human below the discomplete lesion. The volitional electrical potential is used by the system and method to generate a control signal, where the control signal is a function of the volitional electrical potential. That control signal is in turn applied to a plant that comprises at least in part human muscle. In another aspect, the volitional electrical potential is collected via an electrode. In still other aspects, the volitional electrical potential is measured and quantified by the controller and the measurement is used to modulate the control signal output to the plant. In another aspect the control signal is applied to clinically paralyzed human muscle. In yet another aspect the plant further comprises a device in the environment.

BRIEF DESCRIPTION OF THE DRAWINGS

The accompanying figures depict multiple embodiments of a system and method for control using electrical signals recorded from muscles and nerves that are clinically paralyzed. A brief description of each figure is provided below. Elements with the same reference numbers in each figure indicate identical or functionally similar elements. Additionally, the left-most digit(s) of a reference number identifies the drawings in which the reference number first appears.

Figure 1:
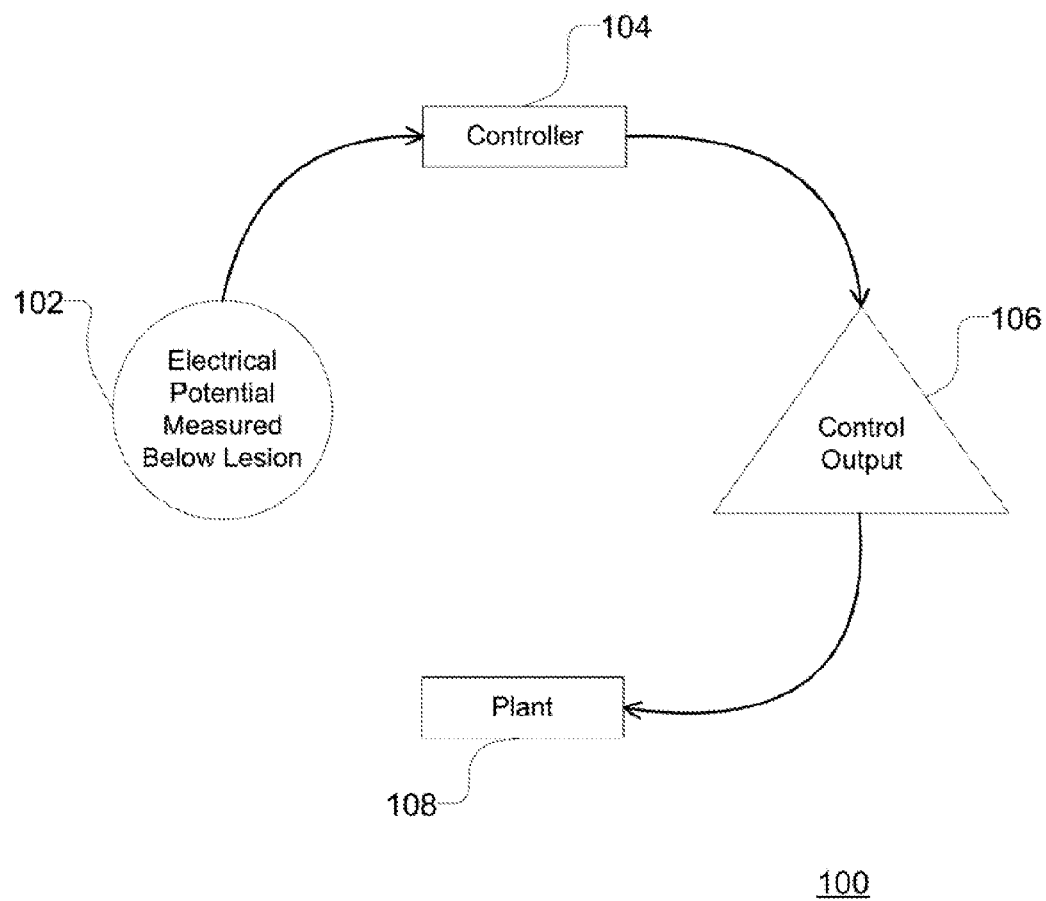
FIG. 1 is a block diagram of the system and method for recording and acting based on electrical signals recorded from a clinically paralyzed muscle.

The present invention is described at least in part with reference to block diagrams and operational flow charts. It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved, including for example executing as asynchronous threads on a processor. Although some of the diagrams include arrows on communication paths to show a primary direction of communication, it is to be understood that communication may occur in the opposite direction to the depicted arrows.

DETAILED DESCRIPTION

Multiple embodiments of a system and method utilizing electrical signals obtained from clinically paralyzed muscle or nerve as a control input are presented herein. Those of ordinary skill in the art can readily use this disclosure to create alternative embodiments using the teaching contained herein.

Lexicon

The following terms used herein have the meanings as follows.

As used herein, the term "discomplete lesion" or "discomplete paralysis" means an injury or damage to the neural pathway between the muscle to the brain, such as that typified by a Spinal Cord Injury (SCI) or those that arise from a variety of diseases such as amyotrophic lateral sclerosis (ALS) or demyelinating diseases that result in functionally or clinically complete (i.e. no externally observable, volitional, physical motor function below the lesion) paralysis of one or more muscles below the lesion. For example, in the ease of a discomplete lesion causes by an SCI, there may exist at least some neural tissue (i.e. axons) at the lesion thereby allowing subclinical manifestation of some, non-clinically observable volitional control below the lesion. In one example, a discomplete SCI results in a person being unable to cause a muscle innervated below the lesion to contract in a physically observable manner, however, since it is a discomplete lesion, sufficient volitional control exists to cause measurable myoelectric signals or measurable signals within the peripheral nerves, such measurable signals manifest below the lesion and controlled by the person with the discomplete lesion are referred to as volitional electrical potentials.

As used herein, the term "electrode" means an operable connection to a muscle or nerve that allows an electrical potential to be recorded or applied. An electrode can be further described by its location . . . i.e. internal, external or percutaneous; electrical or other recording characteristics . . . i.e. unipolar, bipolar, laplacian, magnetic or optical; and with respect to internal electrodes by its placement . . . i.e. intramuscular, epimysial, or nerve, As used herein, when the term "function" is used to describe a relationship between one variable or parameter and a second variable or parameter, the relationship so described is not considered to be an exclusive relationship unless expressly stated, rather the other variables or parameters that are not mentioned or described but that are known to those of ordinary skill in the art may also have a functional relationship to the second variable or parameter. By way of example, if x is described as a function of y the statement is not intended to limit x's value to only being described by y unless expressly slated, rather the variable x may also be a function of other variables (e.g. $x=f(y,t)$.

As used herein the term "computer component" refers to a computer and elements of a computer, such as hardware, firmware, software, a combination thereof, or software in execution. For example, a computer component can include by way of example, a process running on a processor, a processor, an object, an executable, an execution thread, a program, and a computer itself. One or more computer components can in various embodiments reside on a server and the server can be comprised of multiple computer components. One or more computer components are in some cases referred to as computer systems whereby one or more computer components operate together to achieve some functionality. One or more computer components can reside within a process or thread of execution and a computer component can be localized on one computer or distributed between two or more computers.

An "operable connection" is one in which signals or actual communication flow or logical communication flow may be sent or received. Usually, an operable connection includes a physical interface, an electrical interface, or a data interface, but it is to be noted that an operable connection may consist of differing combinations of these or other types of connections sufficient to allow operable control.

As used herein, the term "signal" may take the form of a continuous waveform or discrete value(s), such as electrical potentials, electrical currents, magnetic fields, optical fields, or digital value(s) in a memory or register, present in electrical, optical or other form.

The term "controller" as used herein indicates a method, process, or computer component adapted to affect a plant (i.e. the system to be controlled or effected).

The term "state" as used herein refers to a set of variables that define the characteristics of a particular system in a specific combination. In one non-limiting example, the state of a single axis, hinged joint is expressed as a vector comprised of the current angle, angular velocity and angular acceleration. In other aspects the state of a system includes otherwise unmeasureable or practically unobservable values.

To the extent that the terra "includes" is employed in the detailed description or the claims, it is intended to be inclusive in a manner similar to the term "comprising" as that term is interpreted when employed as a transitional word in a claim.

To the extent that the terra "or" is employed in the claims (e.g., A or B) it is intended to mean "A or B or both". When the author intends to indicate "only A or B but not both", then, the author will employ the term "A or B but not both". Thus, use of the term "or" in the claims is the inclusive, and not the exclusive, use.

System and Method of Control

The present system and method is typified in the block diagram shown to FIG. 1. A discomplete neural controller 100 receives at least in part a command signal from a volitional electrical potential measured below an SCI lesion, referred to as a volitional electrical potential 102. The volitional electrical potential 102 is manifest as electrical potential created in peripheral nerves below the lesion or as myoelectric signals within a muscle that is innervated below the lesion, which in either case do not otherwise manifest as clinically meaningful motion of the muscle.

The volitional electrical potential 102 is received by a controller 104 via an operable connection to an electrode adapted to measure the volitional electrical potential 102. As known to those of ordinary skill in the art typically an electrode is applied to either the muscle or the nerve or in the vicinity of either of the foregoing. The electrode is used to probe the volitional electrical potential 102 present in either the nerve or the muscle. In one embodiment the electrode is directly connected to the controller 104 and the controller 104 possesses a means for measuring the electrical potential. In one embodiment, the controller 104 means for measuring the volitional electrical potential 102 includes a high impedance input amplifier. In other embodiments the controller 104 means for measuring the volitional electrical potential 102 further comprises analog or digital filters that are adapted to attenuate electrical potential not associated with the volitional electrical potential 102. In still another embodiment the controller 104 means for measuring the volitional electrical potential 102 further comprises an analog to digital (A/D) converter for converting an analog measurement of the volitional electrical potential 102 to a digital representation suitable for processing by a digital computer component. In other alternative embodiments, the electrode is an active electrode with either analog signal processing or analog signal processing and A/D conversation incorporated into the body of the electrode itself in these other alternative embodiments, the controller 104 is adapted to accept the processed signal front the active electrode.

In yet another embodiment, a distributed sensor module as typified by the sensor modules disclosed in U.S. Pat. No. 7,260,436 to Kilgore, et. al., is operably connected to the electrode to measure the volitional electrical potential 102. The distributed sensor module in one aspect incorporates analog signal processing and A/D conversion suitable to convert the volitional electrical potential 102 to a digital signal. The digital signal is then useable by other sensor modules that when networked together enable a controller 104 to be distributed across or around the user's body.

In still other embodiments measurement electrodes that do not rely upon direct conduction of electrical potential are used to detect the volitional electrical potential 102. For example, in one non-limiting embodiment, an electrode that uses a magnetic field sensor estimates the volitional electrical potential 102 manifest in the muscle or the peripheral nerve. In another example, an electrode comprising a fiber optic sensor utilizes optical sensing to estimate volitional electrical potential 102. In this case the controller 104 is adapted to accept the optical signals generated in response to the volitional electrical potential 102. As can be appreciated by those of ordinary skill in the art, the discomplete neural controller 100 is readily adapted to using a variety of different electrodes, regardless of the specific sensing method, (i.e. conductive, nonconductive, optical, magnetic etc.) used to measure the volitional electrical potential 102.

The controller 104 uses the measured volitional electrical potential 102 as a command signal from the user indicative of the user's desired action. As can be appreciated by one of ordinary skill the command signal may comprise a simple binary, on/off command. The controller 104 thus maps a baseline or quiescent volitional electrical potential 102 to an on or off state while the complimentary state is mapped to an active or elevated volitional electrical potential 102. In other embodiments the command signal may comprise a graduated response where the characteristics of the volitional electrical potential 102, such as total power, peak power, or frequency is used to create a graduated command signal. In one embodiment, the total power of the volitional electrical signal 102 is mapped by the controller 104 onto a set of live command states. In this manner the user is able to apply graduated commands to the controller 104. In other embodiments the command signal is a combination of one or more volitional electrical signal 102. In still other embodiment the command signal is a combination of volitional electrical signals 102 in combination with other sensor inputs. In yet another embodiment, a series of volitional electrical signals 102 that are temporally related are used to create the command signal. In one embodiment a series of volitional electrical signal 102 pulses within a specific time frame are mapped to a specific command signal. Various command signal generation embodiments are described in greater detail below.

Still referring to FIG. 1, the discomplete neural controller 100 includes a control output 106 that is operably connected to the controller 104. The control output 106 accepts the command signal generated by the controller 104. The control output 106 is operably connected to the plant 108 and generates a control signal adapted to be applied to the plant 108. The plant 108 in one embodiment, i.e. a neural prosthesis embodiment, is a muscle, below the lesion, that is otherwise clinically paralyzed. In which case, the control signal generated by the control output 106 is a series of charge balanced electrical pulses adapted to be applied to the muscle via an electrode to cause the muscle motor units to contract thereby eliciting a functional motion of the otherwise paralyzed muscle. In another embodiment the plant 108 comprises an external device such as an active orthosis or prosthetic device that responds to the control output 106. In another embodiment, the plant 108 comprises an assistive or rehabilitative device in the environment, such as a home automation control, remote control, remote light switch, power wheel chairs, communication devices, or other devices designed to remotely activate or otherwise assist the user with activities of daily living. In another embodiment, the plant 108 is any device that is adapted to accept digital communication such as a home automation controller or computer system.

As used herein, the discomplete neural controller 100 refers generally to a controller that is activated by a volitional electric potential 102 that in turn interfaces with and applies a signal to any plant 108. The plant 108 may comprise a single device or muscle or multiple devices or muscles. If the plant 108 comprises at least one muscle, then the discomplete neural controller 100 may be referred to as a neural prosthesis with no lack of generality.

Fully Implanted System Discomplete Neural Prosthesis

Figure 2:
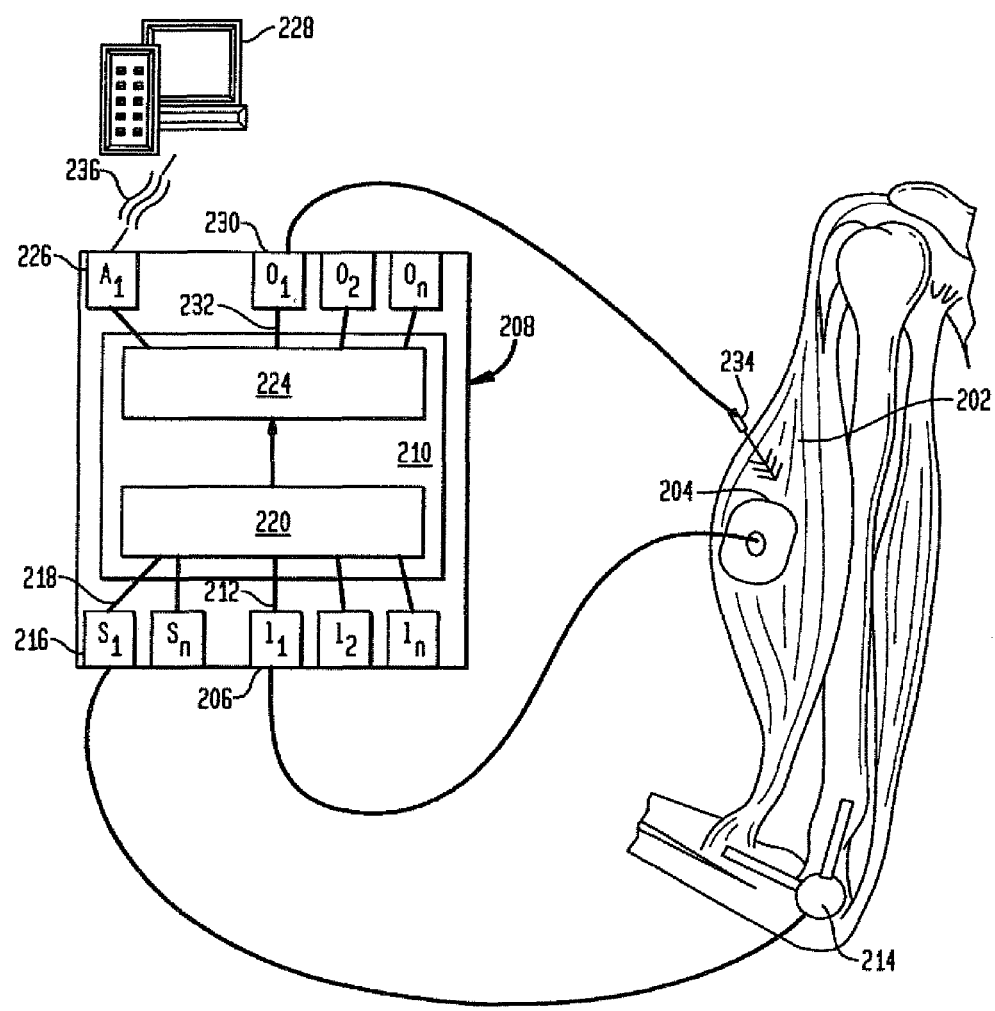
FIG. 2 is an. example of an embodiment of the system and method applied to an upper arm.

Referring now to FIG. 2 an exemplary embodiment of the discomplete neural controller 100 applied to an isolated biceps muscle is presented, as described above, the discomplete neural controller 100 is also referred to as a discomplete neural prosthesis. In this exemplary embodiment an implanted neural prosthesis 200 is depicted. The implanted neural prosthesis 200 is used to measure a volitional electrical signal 102 manifest in the biceps muscle 202 that would otherwise be clinically paralyzed because the nerves that innervate the muscle are below a lesion in the nervous system that results in a discomplete neural lesion. In this embodiment the volitional electrical signal 102 is picked up from the muscle via an epimysial electrode 204 that is affixed to the body of the biceps muscle 202. The epimysial electrode 204 is operably connected to an input $I_1$ 206. The input $I_1$ 206 is in the embodiment depicted is incorporated in a controller module 208.

The implanted, neural prosthesis 200 is implanted within, the user's body, thereby allowing the operable connection between the epimysial electrode 204 and the input $I_1$ 206 to be made via a conductive wire as known to those of ordinary skill in the art. The input $I_1$ 206 is adapted to measure the volitional electrical signal 102 via the epimysial electrode 204 as manifest in the body of the biceps muscle 202 by the user. As known to those of ordinary skill in the art, the input $I_1$ 206 in this embodiment embodies an analog front end that is adapted to filter and amplify the volitional electrical signal 102 while minimizing any change to the volitional electrical signal 102 due to the measurement itself. In one embodiment, the input $I_1$ 206 incorporates a bandpass filter with lower cutoff of about 10 Hz and higher cutoff of about 1 kHz. The input $I_1$, is 206 in the embodiment depicted further comprises an analog to digital (A/D) converter adapted to receive the volitional electrical signal 102 and convert if into a digital representation thereof the digital volitional signal 212.

In the embodiment depicted a secondary source of information is provided by a joint angle sensor 214 that is implanted in the elbow joint. The joint angle sensor 214 is operably connected to a sensor input $S_1$ 216 that accepts the raw signal from the joint angle sensor 214, performs necessary analog signal filtering, amplification and processing and converts the joint angle sensor 214 signal to a digital joint angle signal 218. The joint angle sensor 214 is one exemplary embodiment of what is generally referred to as state measurement or state estimation sensors. These sensors are used to measure or estimate user states or environmental states or a combination thereof that are indicative of the user's body state or configuration and the environment surrounding the user.

The digital volitional signal 212 and the digital joint angle signal 218 are in turn used by the controller 104 to estimate the command desired by the user of the system. In the implanted neural prosthesis 200, the controller computer component 210 is adapted to receive the digital volitional signal 212 and the digital joint angle signal 218. The controller computer component 210 is in this embodiment housed within the controller module 208.

The controller computer component 210 comprises two logical components, a command generation component 220 and an output control component 224. The command generation component 220 and the output control component 224 in the embodiment depicted in FIG. 2 are both logical components of the controller computer component 210. As is appreciated by one of ordinary skill in the art the command generation component 220 and output control component 224 are capable of residing in physically distributed modules that are located in different parts of the user and networked together.

The command generation component 220 comprises an algorithm adapted to estimate the user's desired command based at least in part on the digital volitional signal 212. In the embodiment depicted in FIG. 2, the command generation component 220 is adapted to receive both the digital, volitional signal 212 and the joint angle signal 218. The command generation component 220 generates a digital command signal 222 in response to the digital volitional signal 212 and the joint angle signal 218. In one exemplary embodiment, the digital volitional signal 212 is used to as an on/off or logical signal. In this embodiment the volitional electrical potential 102 created by the user, and digitized by the input $I_1$ 206 to create a digital volitional signal 212 is processed to determine whether the user has exceeded a threshold value (i.e. a logical state change). Once the user exceeds the threshold value, the command generation component 220 interprets this as the user requesting a change in logical state. In the embodiment depicted where the command generation component 220 generated a command signal 222 based on both digital joint angle signal 218 as well as the digital volitional signal 212, the interpretation of the change in digital volitional signal 212 across the logic threshold is adjusted according to the digital joint angle signal 218. In one exemplary embodiment, if the digital joint angle signal 218 is within a first range of angles, the change in digital volitional signal 212 indicating a logical state change is interpreted to be a request to actuate an external device while the same logical state change from the digital volitional signal 212 occurring when the digital joint angle signal 218 is in a different joint angle range results in a command to actuate specific muscles to create functional movement.

The command generation component 220 is operably connected to the output control component 224 and the output control component 224 is adapted to receive the command signal 222. The command signal 222 provides instructions to the output control component 224 on the user's desired commands. The output control component 224 then maps the command signal 222 onto controller module 208 outputs.

In the embodiment of the controller module 208 depicted in FIG. 2, two types of outputs are present. One output is a device output As 226 that is adapted to be coupled to an external device. In the embodiment depicted in FIG. 2 the external device is a television remote control 228 that is coupled to the device output At 226 at least in part by an electromagnetic signal. In the embodiment depicted in FIG. 2, where the controller module 208 is fully implanted, the external command connection 236 is at least partially wireless allowing a signal to pass from inside the user's body to an external device. For example, the external command connection 236 in one embodiment is an inductively coupled link, in another embodiment is a short range, radio-frequency link. The device output $A_1$ 226 is readily adapted by one of ordinary skill in the art to actuate other external devices, such as active orthotic devices, lights, or computer systems. The second output is a stimulator output $O_1$ 230. The stimulator output $O_1$ 230 is operably connected to the biceps muscle 202 via a stimulating electrode, in this ease an intramuscular electrode 234 and is adapted to generate stimulus patterns that cause the biceps muscle 202 to contract.

The mapping component or output control component 224 determines and generates a control signal 232 to output the appropriate signals from the controller module 208 to achieve the users desired functional action. For example, in the foregoing embodiment, the control signal 232 applied to the device output $A_1$ 226 is a command to increment the channel upwards or a specified level of muscle stimulation output via the stimulator output O1 230 to the biceps muscle 202 via the intramuscular electrode 234. In another embodiment the output control component 224 maps the command signal 222 to the control signal 232 to be applied to the biceps muscle 234 based on a stimulation map that is created using clinical procedures that map stimulation parameters onto command signals 222.

As appreciated by one of ordinary skill in the art, the discomplete neural controller 100 is readily adapted by one of ordinary skill in the art to control a combination of one or more muscles, and one or more external devices using a combination of volitional electrical potential 102 and other sensors such as joint angle sensors, gravity vector sensors, force or pressure sensors.

In the embodiment depicted in FIG. 2, the volitional electrical potential 102 created by the user either in the same muscle or muscle that is proximate to the that is stimulated via the intramuscular electrode 234. In the embodiment of the implanted neural prosthesis 200 depicted in FIG. 2, the myoelectric signal is the volitional electrical potential 102 that is generated by the user. In other embodiments, combinations of voluntary myoelectric signals (i.e. generated by the user above the lesion) are combined with one or more volitional electrical potentials 102 to provide signals or input to the command generation component 220.

Generating Command Signals

As introduced in the exemplary embodiment of an implanted neural prosthesis 200 described above, a command signal 222 is generated by the command generation component 220 based on inputs received by the command generation component 220 from the user's volitional electrical potential 102 (via Input $I_1$ 206) and other environmental information from environmental and state sensors, such as the joint angle sensor 214 via the sensor input $S_1$ 216. The command generation component 220 in various embodiments outputs a variety of different command signal types. The command signal types include triggering signals (on/off or logic signals and triggering of complex patterns), force or modulated level information, and combinations of both. Thus the command generation component 220 operates to intuit the desires of the user based on the user's volitional electrical potential 102 and other information, including information about the user's environment, body state, and other inputs such as voice or other inputs that are not impacted by the discomplete neural lesion. A description of these various command signal types is provided in relation to specific functional tasks.

Augmentation Control Mode

In an augmentation control mode the, discomplete neural controller 100 operates to enhance the volitional commands that the user is otherwise applying to a muscle to create a functional movement. In another aspect, the discomplete neural controller 100 operates to activate nearby muscles that have a functionally similar motion to the muscle where the user is able to volitionally elicit recordable EMG activity.

For example, in the case of shank extension, the user may have the ability to create a volitional electrical potential 102 in one head of the quadriceps muscle, but is unable to either contract that head of the muscle in a functional manner or illicit volitional electrical potential 102 in the other beads of the quadriceps. When operating to augment the user's latent volitional commands, the discomplete neural controller 100 measures the volitional electrical potential 102 created by the user when the user attempts to extend the shank. The measured volitional electrical potential 102 is interpreted by the system as a command to contract the quadriceps muscle, with specifics regarding commanded force and output signal to the stimulated head(s) of the quadriceps dictated by the controller 104.

One exemplary operational mode for a discomplete neural controller 100, presented in view of the implanted neural prosthesis 200 embodiment, is a stimulus augmentation mode. In this mode the user generates a volitional electrical potential 102 in the muscle to be stimulated, in the case of the embodiment depicted in FIG. 2, the biceps muscle 202. As described above, a digital volitional signal 212 is generated that corresponds to the volitional electrical potential 102 created by the user. The command generation component 220 then processes the digital volitional signal 212 to estimate the force desired by the user. The force desired by the user as estimated by the controller 208 via the digital volitional signal 212 is used to adjust the command signal 222 accordingly. For example, in the stimulus augmentation mode, the controller 208 detects in increase in volitional electrical potential 102 caused by the user attempting to move the functionally paralyzed limb. The controller 208 uses the digital volitional signal 212 to determine whether to increase the stimulus pulse applied to the biceps muscle 202 or decrease the stimulus pulse based on the digital volitional signal 212.

In another embodiment the biceps muscle 202 is mapped to define maximum and minimum stimulus parameters and sensitivity to changes in the stimulation pattern (i.e. adjustments to pulse width, interpulse interval, pulse height etc). The increase or decrease in the digital volitional signal 212 is also mapped to determine the maximum volitional electrical potential 102 the user is capable of generating. Then the controller 208 utilizes a proportional difference between the maximum and actual volitional electrical potential 102 and the mapped stimulation parameters to generate a command signal 222 for the stimulation pattern output to the biceps muscle 202 that is mapped proportionally to the volitional electrical potential 102 commanded by the user.

Sample and Stimulate

Referring again to the embodiment of the implanted neural prosthesis 200 depicted in FIG. 2, the measurement or sampling of the volitional electrical potential 102 in the presence of muscle stimulation is detailed. There are multiple methods known to those of ordinary skill in the art for sampling and stimulating on the same muscle or muscles that are nearby where stimulation of the muscle causes saturation of the myoelectric signal on the unstimulated muscles.

Figure 3:
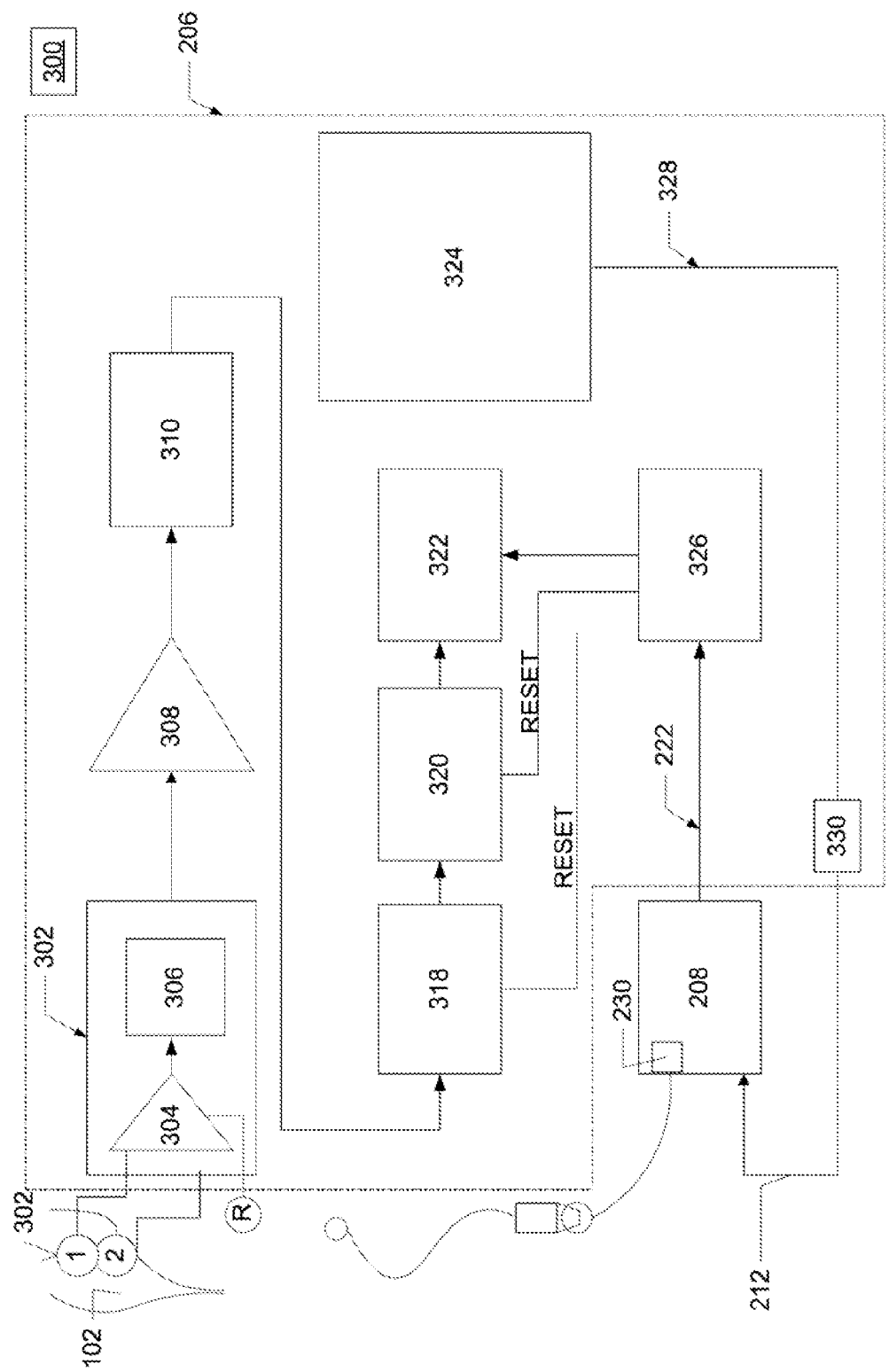
FIG. 3 is a block diagram of a signal processing circuit for sampling volitional electrical potential in the presence of stimulation artifacts.

For exemplary purposes, one system and method for obtaining volitional electrical potential 102 from a muscle in the presence of stimulation artifacts is described by referring to the sampling block diagram provided of FIG. 3. A block diagram of a sampling circuit 300 adapted to record myoelectric signals generally and more specifically volitional electrical potential 102 signals in the presence of stimulation artifacts is detailed. As appreciated by one of ordinary skill in the art, the sampling circuit 300 implemented in the implanted neural prosthesis 200 embodiment of a discomplete neural controller 100 incorporates the sampling circuit as part of the input $I_1$ 206. Thus the input $I_1$ 206 is adapted to provide sampling around the stimulation output by the stimulator output $O_1$ 230 to the muscle via the intramuscular electrode 234. The sampling circuit 300 details the differential reference electrodes of the epimysial electrode 204 as a pair of two differential EMG recording electrodes 302 and the reference electrode 304.

The volitional electrical potential 102 recorded by the EMG recording electrodes 302 and reference electrode 304 are input to the pre-amplifier component 306. The pre-amplifier component 306 in the embodiment depicted incorporates a differential amplifier 308 and a bandpass filter 310. The bandpass filter 310 has in one embodiment a low frequency cut off of about 300 Hz and a high frequency cut off of about 1000 Hz. In other embodiments the bandpass filter 310 cutoff frequencies are selected by one of ordinary skill in the art to reduce 60 Hz noise, high-frequency signals from the hospital and medical environments and recharge artifact created by the stimulation of the muscle. The pre-amplified signal is then amplified via an amplifier 312 and then rectified via a full-wave rectifier 314 before entering the sampling and filtering circuit 316.

The sampling and filtering component 316 is comprised of a series cascade of an analog switch 318, and integrator 320 a sample and hold circuit 322 and an adaptive filter 324. A timing component 326 is used to select the portion of the volitional electrical potential 102 signal present between stimulating pulses. In one exemplary embodiment when stimulating pulses are delivered with a minimum of about 45 ms between stimulation bursts, the timing component 326 is used to sample the volitional electrical potential 102 only during the last about 35 ms between the stimulating pulses. The integrator 320 is reset betweens stimulating pulses by the same timing component 326. The signal output from the integrator 320 is output to a sample and hold circuit 322 that in turn is connected to the adaptive filter 324.

In the embodiment depicted two separate adaptive filter 324 embodiments are used. In one embodiment an adaptive time constant filter with a first order low pass filter where the time constant is varies as a function of the derivative of a fixed time constant parallel filter. The parallel filter in one aspect is a second order Butterworth filter with a time constant of 250 ms that allowed the time constants of the adaptive fitter to range between 60 ms to 1.2 ms. The output of the adaptive filter 324 is an analog command signal 326 that corresponds to the volitional electrical potential 102 measured between muscle stimulating pulses. The volitional signal 326 is sampled via an analog-to-digital converters 330 to generate the digital volitional signal 212 that is used the command controller module 208 to generate the command signal 222 which in turn is used by the timing component 326 to coordinate sampling.

In the second embodiment an adaptive step-size or slew rate limiting filter is used for the adaptive filter 324. In this second embodiment, each time the stimulus command to the muscle is updated, a comparison is made between the current command signal 222 and the command signal 222 during the previous stimulation update. The allowable step size (slew rate) is started at a minimum value and the actual command is moved toward the desired command by no more than the allowable step size. With each successive step size in the same direction (i.e. increase or decrease the command signal 222) the stepsize is increased exponentially up to the maximum, step size. Each time the step direction, changes, the step size is reset to the minimum valise.

As appreciated by one of ordinary skill in the art, in alternative embodiments of the discomplete neural controller 100 the volitional electrical potential 102 is obtained from non-involved muscles or nerves where stimulation related artifacts are either significantly attenuated or are undetectable. Thus in alternative embodiments the volitional electrical potential 102 sampling process is not required.

Triggering

In another control mode of the discomplete neural controller 100, the volitional electrical potential 102 is used by the controller 104 as a logical control input. A logical control or triggering command resembles a digital logic or on/off signal. In the ease of a volitional electrical potential 102, the on/off signal is tailored to change state upon the user applying the volitional electrical potential 102.

The volitional electrical potential. 102 used for triggering is processed, which in the case of a volitional electrical potential 102 not impacted by stimulus artifacts (i.e. no stimulus is output such as where the controller is used to only control an external plant 108 and not simulate muscle or where the stimulated muscle are isolated from the measured volitional electrical potential 102). In these embodiments, rather then using the sampling circuit 300 described above traditional analog filtering and amplification is used to amplify and remove noise from the volitional electrical potential 102. The signal characteristics of the volitional electrical potential 102 is then used by the controller 104 to determine if the user has created a large enough volitional electrical potential 102 to cause the state of that channel to switch from the baseline or no potential to the complimentary state (i.e. from on to off or visa versa).

The volitional electrical potential 102 is evaluated by the controller 104 rising a variety of means to estimate the signal characteristics. One or more signal characteristics of a volitional electrical potential 102 are suitable for mapping into a measurable signal. In fact, different volitional electrical potentials 102 collected from different muscles or nerves may have different characteristics due to the number and quality of axons that actually cross the lesion. In one embodiment, the total energy of the volitional electrical potential 102 is calculated by integrating either the rectified signal or the signal squared over a fixed period of time. In another embodiment, a windowed Fourier transform, or digitally implemented fast Fourier transform (FFT) is used to estimate both frequency characteristics as well as signal energy during the fixed interval. In yet another embodiment a time-frequency analysis or wavelet, analysis is used to gather the time-varying characteristics of the volitional electrical potential 102. In one mode the user is required to told a volitional electrical potential 102 greater than a threshold value for multiple sampling windows in order to ease the controller 104 to identify a trigger command. In the above analysis techniques a baseline volitional electrical potential 102 mapping is used to calibrate the discomplete neural controller 100.

The initial mapping process for identifying muscles and nerves where a user is capable of generating measurable, but still sub-functional, volitional electrical, potential 102 is an initial starting point for tailoring the discomplete neural controller 100 for a variety of users. Specifically, one of the initial steps to the process is identifying which muscles and nerves of the user are still controlled by the user and capable of generating volitional electrical signals 102. This initial screening in one embodiment is performed pre-operatively using surface EMG recording electrodes or percutaneous needle electrodes to measure volitional electrical signals 102 generated by the user. In this manner muscles and nerves that are still partially under the volitional control of the user are identified and the amount offered and other characteristics of the user's volitional electrical potential 102 are initially characterized. After identification of candidate muscles and nerves, systems with implanted electrodes are implanted and the user's volitional electrical potential 102 is again characterized. After the completion of this characterization process it is possible to create mapping functions that allow the controller 104 to identify and characterize a user's volitional electrical potential 102.

The characterization process for the user's volitional electrical potential 102 is initiated by having the user attempt to 'move' a particular paralyzed limb or muscle. The discomplete neural lesion results in no clinical movement of the limb, however the user may generate a volitional electrical potential 102. The resulting volitional electrical potential 102 is initially characterized based on having the user attempt to move the limb or generate a desired force level. In one embodiment the user is simply asked to generate maximal force. In other embodiments, the user is presented a real-time feedback of the volitional electrical potential 102 levels allowing the riser to attempt to control to desired marks. During the characterization process, the volitional electrical potential 102 is recorded and characterized to estimate the total force the user is able to generate and assess the ability of the user to generated graduated or various levels of control. The characterization information is used to customize a particular controller 104 and more specifically a command generation component 220 to a given user's ability to generate volitional electrical potential 102 in muscles and nerves based on the type of actuation available to the user.

Referring again to the case of a triggering input, the triggering input determines whether or not to switch the state of the command signal from an initial state to a second state. In one embodiment, the initial state is a default state of the toggle switch (e.g. 0) corresponds to a baseline or no volitional electrical potential 102 generated by the user while the complimentary state (e.g. 1) corresponds to an elevated level of volitional electrical potential 102, thus when the volitional electrical potential 102 returns to baseline or zero level the toggle switches back to the default state (e.g. 0). In another embodiment the triggering input causes only a state change from its current state to the next state (i.e. in the case of a binary switch toggling to the other state—e.g. from a 1 to a 0 or visa versa).

In embodiments with multiple state switches, when the volitional electrical, potential 102 exceeds the trigger state the switch state increments by a fixed amount (i.e. moving from the current mode to another mode). For example, in one aspect the switch state may possess three separate modes of operation, a first state corresponding to no stimulus, a second state corresponding to a specific grasp pattern (e.g. palmar grasp) or other action applied to the plant 108, and third state corresponding to a second grasp pattern (e.g. lateral grasp) or other action applied to the plant 108.

In other embodiments, multiple inputs are used by the controller 104 to determine the user's desired action. In one exemplary embodiment, a first volitional electrical potential 102 signal is used as a toggle input, where the action of the first volitional electrical potential 102 signal is used to toggle the state of the controller 104 from mode to mode, such as the exemplary grasp mode controller described in the preceding paragraph. Then a second volitional electrical potential 102 signal is used by the controller to adjust the force desired for the grasp. In this embodiment, each discrete pulse by the user of the second volitional electrical potential 102 would cause the controller 104 to interpret the user as requesting the force to be increments from the current force level to the next force level. One of ordinary skill in the art can adapt the forgoing exemplary embodiment to scenarios with multiple volitional electrical potential 102 signals or other EMG or external input devices (e.g. joysticks, buttons, voice input, etc.).

Sequence Triggering

In another exemplary embodiment, the controller 104 utilizes the volitional electrical potential 102 created by the user, in some cases in conjunction with other inputs such as EMG signals or input devices to select, initiate and modulate predefined sequences of commands. For example, in an embodiment of the discomplete neural controller 100 applied to functional walking, the user may first select and walking mode for the controller 104. In the walking mode, the controller 104 is interpreting volitional electrical potential 102 signals as being indicative of the user's desired action (e.g. lifting a leg, stopping the gait cycle, transfer of weight, etc). Thus, when the volitional electrical potential 102 signal or signals from volitional electrical potential 102 are received the controller 104 interprets the volitional electrical potential 102 as being indicative of the user requesting the next step in the sequence or modulating the sequence. In one example, for a walking mode of the discomplete neural controller 100 used for lower extremity functional motion, the volitional electrical potential 102 signal from the user is interpreted by the discomplete neural controller 100 to initiate the next sequence of commands for lifting a leg. Thus an entire series of command signals 222 are initiated by a volitional electrical potential 102 from the user.

Estimation of User Commands

The discomplete neural controller 100 uses at least in part volitional electrical potential 102 information to estimate the user's desired commands. As described in relation to the embodiment of an implanted neural prosthesis 200, a command generation component 220 accepts the measured volitional electrical potential 102 generated by the user and measured by the Input It 206 to the controller module 208 (i.e. the digital volitional signal 212) as part of its input. The command generation component 220 also accepts in other embodiments inputs such as state measurement information from sensors in the user or other user actuated information (including signals from other parts of the user's body above the lesion) as well as information or knowledge of the controller's 104 internal state and control output 106 state to estimate the user's desired commands. The user's estimated or desired commands are then output as a command signal 222 to the output control component 224 that outputs the necessary signals to the stimulation electrodes or other external actuators to achieve the desired result. As is readily appreciated by those of ordinary skill in the art, the command generation component 220 is frequently tailored to the specific training and capabilities of the user and over time the command generation component 220 may be adapted either automatically or manually to adjust the resulting command signal 222.

The command generation component 220 is implemented in the controller 104 to estimate the user's desired command. In one embodiment the command generation component 220 uses a rule-base, heuristic or expert system based approach to interpret the inputs to the command generation component 220 and estimate the user's desired commands and output that as a command signal 222 adapted for input to the output control component 224. In another embodiment a fuzzy logic system is used to classify the inputs and output a command signal 222. In still another embodiment a form of neural network is trained to classify the inputs and output a command signal 222 that reflects the user's desired goals. In other embodiments, combinations of the foregoing are combined and adapted to operate together in order to properly classify the user's desired commands and generate a command signal 222.

The command signal 222 is then accepted by the output control component 224 which in turn generates specific output commands for the stimulated muscles and other devices attached or controlled by the discomplete neural controller 100. In one embodiment the output control component 224 uses an inverse map generated from the user's response to stimulus commands to generate the control signal 232 output via the stimulator output $O_1$ 230. In another embodiment a neural network is trained and used to generate the control signal 232 based on the command signal 222. In still other embodiments, heuristic, rules-based, expert systems or fuzzy logic is used by the output control component 224 to generate the control signal 232. In still other aspects, combinations of the foregoing are used by the output, control component 224 to generate the control signal 232. In still other embodiments, the control signal 232 is further modulated by state information provided by other sensors that measure both internal body states as well as external environment state information.

Exemplary Implementation—Partially Implanted System

Figure 4:
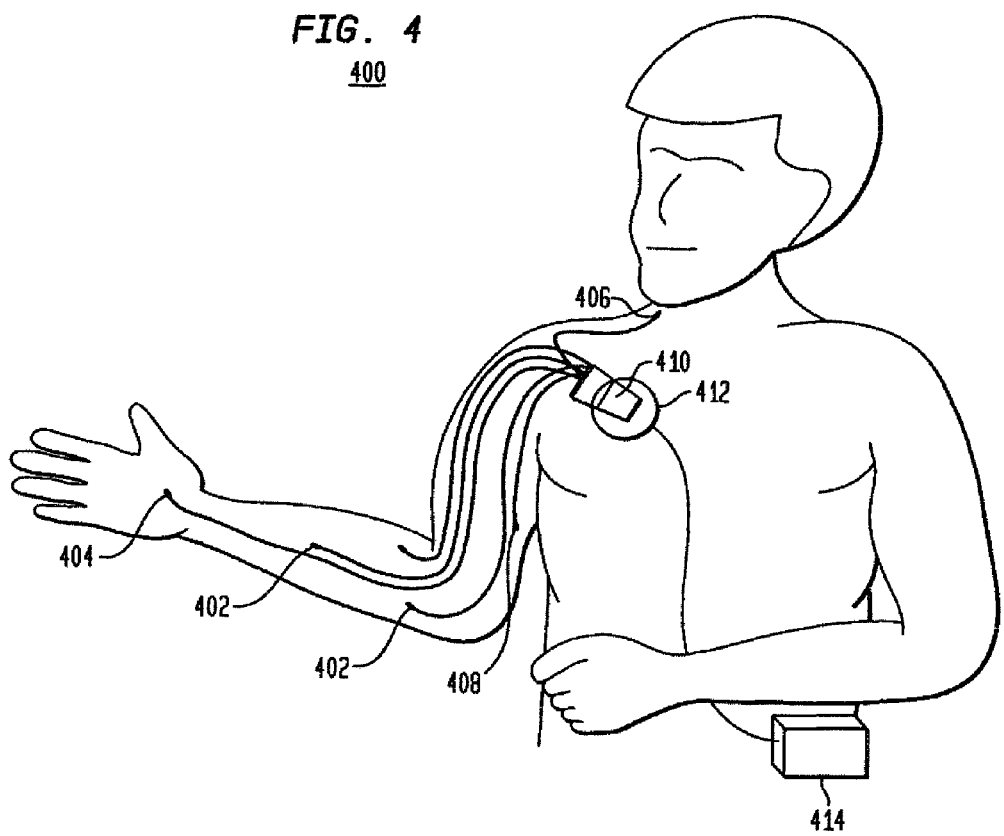
FIG. 4 is a functional illustration of a partially implanted system for controlling upper extremity motion via electrical signals recorded from clinically paralyzed muscles.

Referring now to FIG. 4, an embodiment of the discomplete neural controller 100 is depicted as a partially implanted upper extremity prosthesis 400. The partially implanted upper extremity prosthesis 400 depicted uses multiple stimulating electrodes 402 that are operablely connected to an implanted recording stimulator 412. The implanted recording stimulator 410 is adapted to both receive inputs from either myoelectric or electrical potentials manifest in peripheral nerves. The implanted recording stimulator 410 is connected via an inductive link to an external control unit 414 that is worn on the user's belt. The inductive link in the embodiment depicted is provided via an pair of inductive coils 412 that are operably connected to at one end to the implanted recording stimulator 410 and the external control unit 414 to enable the external control unit 414 to both provide power and communicate with the implanted recording stimulator 412.

The partially implanted upper extremity prosthesis 400 depicted in FIG. 4 includes three separate inputs front the user to provide command information to the controller 104. The first is a recording electrode 404 adapted to record a first volitional electrical potential 102 generated by the user on or in proximity to one of the muscles being stimulated by a stimulating electrode 402. As discussed above, the recording electrode 404 input to the implanted recording stimulator 410 is sampled in order to capture volitional electrical potential 102 signals while avoiding stimulation artifacts from the electrical stimulation delivered via the stimulating electrodes 402. A second, uninvolved recording electrode 406 is placed in an isolated location where the volitional electrical potential 102 is relatively isolated from the stimulating pulses.

The partially implanted tipper extremity prosthesis 400 also includes an implanted switch 408. The implanted switch 408 is placed in a location where the user can actuate the switch using their muscle control by adjusting their shoulders.

The implanted recording stimulator 410 receives the information from the recording electrode 402, uninvolved recording electrode 406 and implanted switch 408. The combination of volitional electrical potential 102 signals and the switch information is initially processed and provided to the external control unit 414 in this embodiment as user generated signals. The external control unit 414 processes the information to estimate the user's desired command that is then turned into control outputs 106 that are passed to the implanted recording stimulator 410 to be issued as stimulus commands to the muscles via the stimulating electrodes 402. As discussed previously, external devices such as a remote lamp or orthotic device are also readily adapted for actuation by the external control unit 414.

As discussed above the external control unit 414 may use multiple combinations of different logic functions to estimate the user's desired command. For example, as discussed above with respect to the embodiment the implanted neural prosthesis the user generated signals are processed by the command generation component 220 to estimate the user's desired commands represented as a command signal 222. Thus, in the embodiment depicted a combination of user inputs that include volitional electrical potential 102 signals and other inputs are used by the command generation component 220 to determine the control output 106. In the embodiment depicted, the input signal from the volitional electrical potential 102 is recorded via the implanted recording stimulator 210. Thus the recording stimulator 210 pre-filters, amplifies and digitizes the volitional electrical potential 102 signals from the recording electrode 402 and the uninvolved recording electrode. The resulting signal is passed to the external control unit 414 where the command generation component 220 resides. In other embodiments, a person of ordinary skill in the art may readily distribute some or ail of the functional elements of the command generation component 220 to the implanted recording stimulator 410 in addition to or in lieu of the external control unit 414.

Exemplary Implementation—External System

Figure 5:
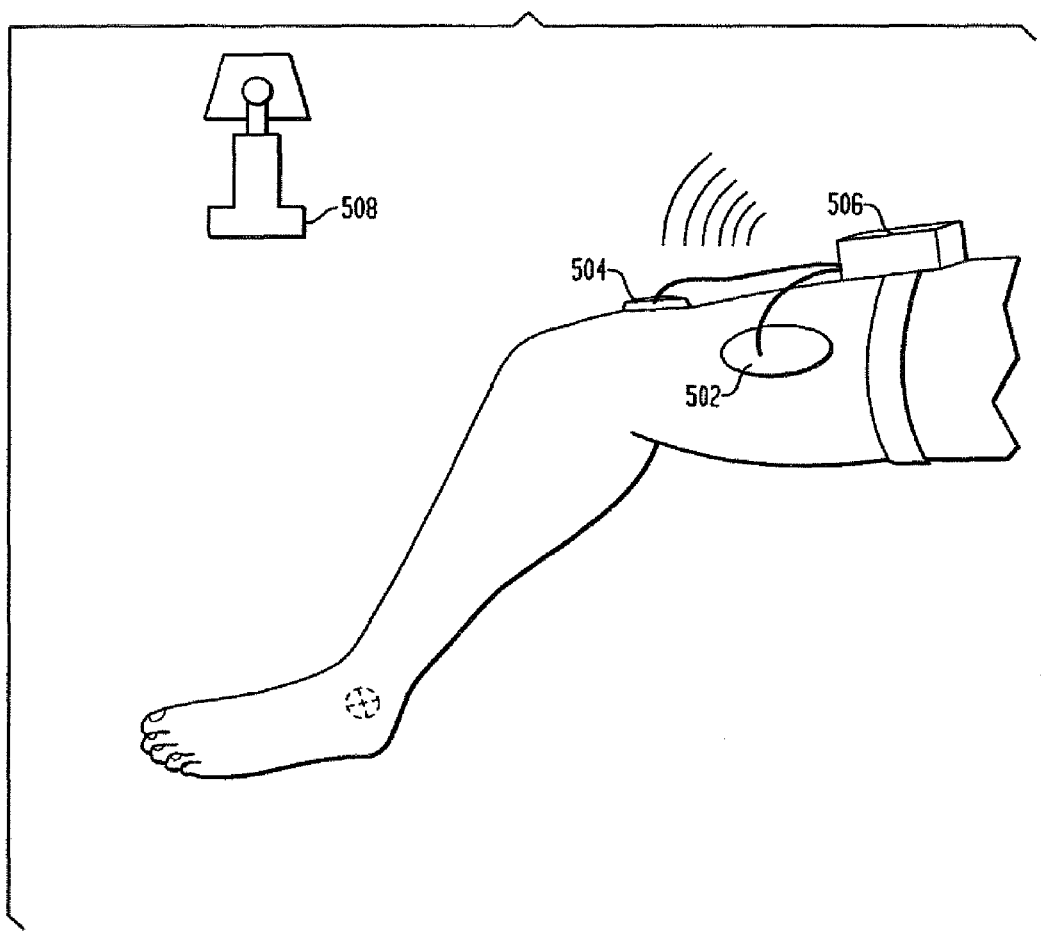
FIG. 5 is a functional illustration of an external system for controlling lower extremity motion via electrical signals recorded from clinically paralyzed muscles.

Referring now to FIG. 5, another exemplary embodiment of a discomplete neural controller 100 is illustrated, in this embodiment an external neural prosthesis 500 is shown. In this embodiment, an external recording electrode 502 is affixed to the surface of the user's leg to record volitional electrical potential 102 signals. In an alternative embodiment not shown, a percutaneous or needle electrode is used to further isolate the volitional electrical potential 102 to a specific muscle and increase sensitivity. The volitional electrical potential 102 is measured by an external controller 506 that receives the volitional electrical potential 102 from the external recording electrode 502. The external controller 506 in this embodiment includes both a command generation component 220 as well as an output control component 224. The volitional electrical potential 102 signals and other signals provided by other inputs and sensors (not shown in FIG. 5), such as gravity sensors, heel strike sensors, or instrumented orthotic braces etc. are also input to the external controller 506. The external controller 506 and more specifically the command generation component 220 of the external controller 506 (not shown in FIG. 5) estimates the user's desired action based on these volitional electrical potential 102 signals and other inputs. The external controller 506 then uses the command signal 222, estimated by the command generation component 220, to the output control component 224 (also not shown in FIG. 5). The resulting control signal is output by the external controller 506 to active an external stimulating electrode 504, in this embodiment a surface electrode. The resulting control signal is also output by the external controller 506 in this embodiment via a wireless signal interface to an remote device 508, in this case a lamp.

Exemplary Volitional Electrical Potential

Figure 6:
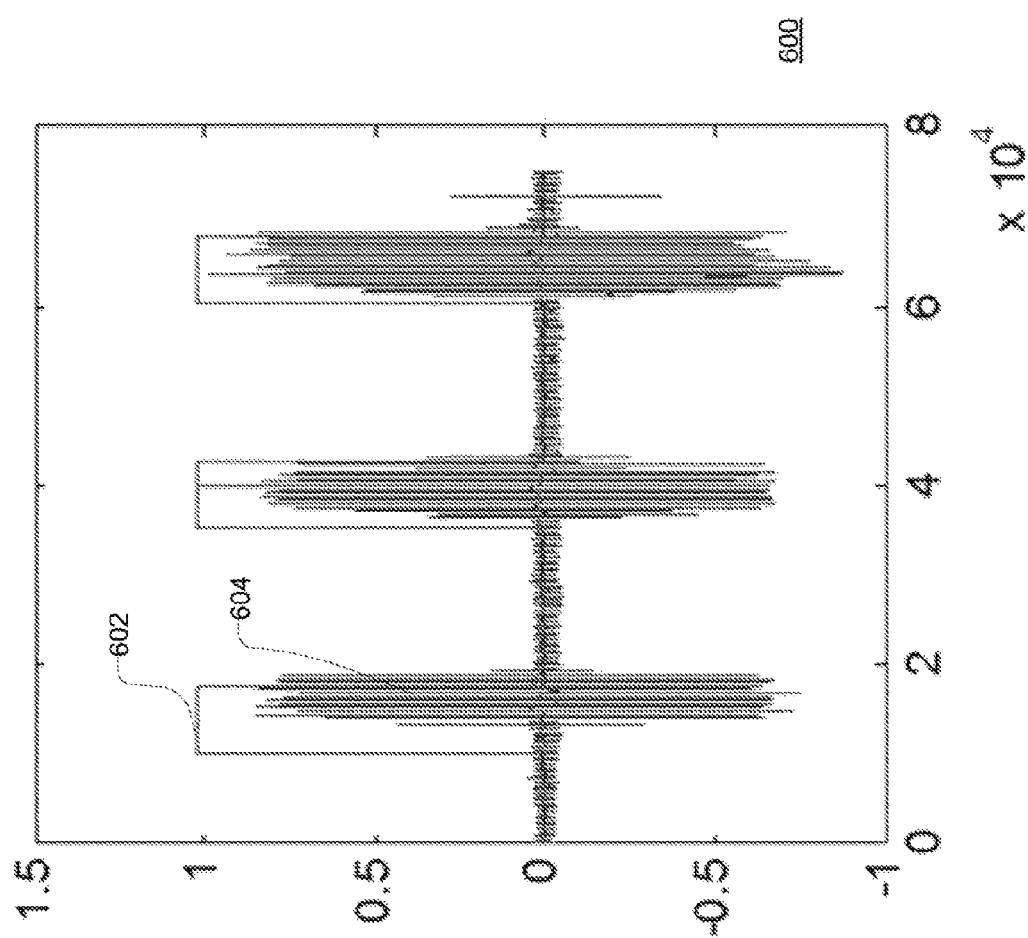
FIG. 6 is a plot showing experimental results of a human with a clinically complete lesion that demonstrates the ability of the user to generate a volitional electrical potential below the lesion.

Referring now to FIG. 6, a plot 600 demonstrating experimental results of a user creating volitional electrical potential 102 signals with a clinically complete lesion caused by an SCI is shown. The plot 600 comprises a reference signal 602 that shows an external prompt provided to the user requesting that the user to generate a volitional electrical potential 102 associated with a paralyzed muscle. The volitional electrical potential 102 is collected with an external recording electrode 504 configured to receive volitional electrical potential 1.02 generated by the user. The plot 600 demonstrates the ability of the user to generate a volitional electrical potential 102 on demand, which in turn is used by the discomplete neural controllers 100 of the present system and method to apply control signals to a plant.

CONCLUSION

While various embodiments of the present system and method for control using electrical signals obtained from functional paralyzed muscles and nerves are described above, it should be understood that the embodiments have been presented by the way of example only, and not limitation, it will be understood by those skilled in She art that various changes in form and details may be made therein without departing from the spirit and scope of the invention as defined. Thus, the breadth and scope of the present invention should not be limited by any of the above described exemplary embodiments.

What is claimed is:

1. A device adapted to use signals from a nervous system of a human, comprising:
   a controller with an input means for generating an input of a volitional electrical potential generated by the human's body below a lesion in the nervous system and an output means for applying a control signal to a plant that is operably connected to said controller wherein said control signal is a function of said input.

2. The device of claim 1, wherein said input means comprises an electrode.

3. The device of claim 2, wherein said electrode is selected from the group consisting of intramuscular, epimysial, percutaneous, or surface.

4. The device of claim 1 wherein said controller further comprises a computer component to estimate a total energy of said volitional electrical potential.

5. The device of claim 4, wherein said control signal output is modulated proportionally as a function of said total energy.

6. The device of claim 1, wherein said volitional electrical potential is measured from a peripheral nerve.

7. The device of claim 1, whereby said input comprises a first volitional electrical potential and a second volitional electrical potential.

8. The device of claim 1, wherein said plant is a device external to the human.

9. The device of claim 1, wherein said control signal creates a functional movement of said plant and said functional movement of said plant is selected by the human via said volitional electrical potential.

10. The device of claim 1, wherein the volitional electrical potential is generated by a nerve of the human body.

11. The device of claim 1, wherein the volitional electrical potential is generated by a muscle of the human body.

12. A neural prostheses for a human, comprising:
   an electrode adapted to receive a volitional electrical potential generated by the human's body and manifested below a lesion in the human's nervous system;
   a controller operably connected to said electrode and adapted to measure said volitional electrical potential, wherein said controller generates a control signal that is a function of said volitional electrical potential; and
   an output operably connected to said controller to apply said control signal to a plant.

13. The device of claim 12, further comprising a command generation component that generates an estimated command that is a function of said volitional electrical potential.

14. The device of claim 13, further comprising an output control component adapted to accept said estimated command and generate said control signal as a function of said estimated command.

15. The device of claim 12, where said controller accepts a state measurement indicative of the human's state whereby said control signal is a function of said state measurement.

16. The device of claim 12, wherein a level of said control signal is modulated as a function of said volitional electrical potential.

* * * * *